United States Patent
Normand et al.

(10) Patent No.: US 6,917,616 B1
(45) Date of Patent: Jul. 12, 2005

(54) METHOD AND APPARATUS FOR REDUCTION AND RESTORATION OF DATA ELEMENTS PERTAINING TO TRANSMITTED DATA PACKETS IN A COMMUNICATIONS NETWORK

(75) Inventors: Dominique Normand, Bruz (FR);
Marc André, Cesson Sevigne (FR);
Didier Malorey, Chevaigné (FR);
Esabel Ambrosio, Chantepie (FR)

(73) Assignee: Alcatel Canada Inc., Kanata (CA)

( * ) Notice: Subject to any disclaimer, the term of this patent is extended or adjusted under 35 U.S.C. 154(b) by 0 days.

(21) Appl. No.: 09/397,849

(22) Filed: Sep. 17, 1999

(30) Foreign Application Priority Data

Sep. 18, 1998 (EP) .......................................... 98 460 038

(51) Int. Cl.[7] .............................................. H04Q 11/04
(52) U.S. Cl. .................... 370/395.1; 370/474; 370/477
(58) Field of Search ................................ 370/389–392, 370/395.1, 474, 477

(56) References Cited

U.S. PATENT DOCUMENTS

| | | | |
|---|---|---|---|
| 5,046,550 A | | 9/1991 | Boll et al. ................... 370/335 |
| 5,406,550 A | * | 4/1995 | McTiffin |
| 5,717,689 A | * | 2/1998 | Ayanoglu |
| 5,745,837 A | | 4/1998 | Fuhrmann .................... 455/5.1 |
| 6,560,206 B1 | * | 5/2003 | Naden et al. ............. 370/310.1 |
| 2001/0025321 A1 | * | 9/2001 | Tang et al. .................. 709/246 |
| 2003/0137995 A1 | * | 7/2003 | Defoort ...................... 370/474 |

FOREIGN PATENT DOCUMENTS

EP        0987917 A1 *  3/2000

OTHER PUBLICATIONS

Aikawa, Satoru et al., Forward Error Correction Schemes for Wireless ATM Systems 1996, IEEE 0–7803–3250–4/96, pp 454–458.*

Raychauduri D., "ATM Based Transport Architecture for Multiservices Wireless Personal Communications Networks"; Serving Humanity Through Communications. SUPERCOMM/ICC, New Orleans, May 1–4, 1994, vol. 1, May 1, 1994, pp. 559–565.

* cited by examiner

*Primary Examiner*—Melvin Marcelo

(57) ABSTRACT

The invention relates to a system and method for the transmission of data organized as cells comprising a header and a payload. In particular, the following steps are taken in the system and method; reducing of the size of at least certain of the headers; for transmission between two communications devices of a network, to form headers that are reduced in size by the elimination of predetermined data elements; and at one of the communications devices, reconstructing the headers to their original size from the reduced headers.

23 Claims, 4 Drawing Sheets

METHOD AND APPARATUS FOR REDUCTION AND RESTORATION OF DATA ELEMENTS PERTAINING TO TRANSMITTED DATA PACKETS IN A COMMUNICATIONS NETWORK

FIELD OF THE INVENTION

The present invention relates generally to a method and apparatus for communications systems which transmit data between two or more network elements, for instance data organized in the form of transmitted packets such as protocol data units (PDUs) of fixed size, wherein data elements pertaining to the transmitted packets are reduced prior to transmission thereof and restored thereafter. The invention relates more particularly, but not exclusively, to such a method and apparatus as deployed in communications systems which make use of fixed length cells in the ATM format.

BACKGROUND OF THE INVENTION

Communications networks which employ ATM (asynchronous transfer mode) techniques are well known. In general, the data elements travel at high bit rates through a network in the form of cells. Each cell has a header field and an information field or payload. The header field is used for the multiplexing or routing of the associated cell through different element of the network (for instance terminals, multiplexers, scramblers, switches and the like). The information field typically comprises useful data destined for a user of the network to whom the cell is addressed.

The two fields mentioned above have a fixed format. The leader field is typically comprised of 5 data bytes and the information field is typically comprised of 48 data bytes Among the 5 data bytes of the header field, there can be distinguished two fields used to identify multiplexing or routing functions namely 8 bits for a virtual path identifier (or VPI) and 16 bits for a virtual channel identifier (or VCI).

In general, transmission techniques or devices which work at relatively high bit rates are available for deployment in an ATM network. Such techniques or devices are available especially for transmission between intermediate nodes within a given network. In contrast, at the edges or boundaries of a backbone network, problems are often encountered in ensuring data distribution on to end users at sufficiently acceptable bit rates. Indeed, the link between the backbone network and a final subscriber is often provided by a telephone line, such that it may be difficult to achieve bit rates of the order of several Mbits/s.

For end links of the kind discussed above which comes to a backbone network, it is possible to utilize DSL modulation, or a derivative modulation such as ADSL, HDSL, SDSL or the like, in order to provide for communications at rates of up to several Mbits/s. However, this may be insufficient for supporting some types of services. It must be noted that apart from the main portion of the bandwidth that is used to convey useful information from the information field or payload of cells, an additional portion of the bandwidth is used to convey the header field of cells. Furthermore, an additional part of the bandwidth must also be reserved for network administration or management functions. For instance, such functions may pertain to the management of the various network elements or devices to which cells are addressed.

Therefore, based on the foregoing, another approach to the optimization of bandwidth would be desirable. McTiffin has proposed a solution to this problem in a special case of RF transmission between an ATM network and a subscriber. This known technique, for instance as described in the U.S. Pat. No. 5,406,550, proposes the elimination of the VPI end VCI identification fields and the use of a radio coding that identifies the addressee. However, this approach may have several drawbacks. First of all, an approach of this kind is intended for radio link transmissions in which the transmitted signals bear an identification of the addressee by way of radio coding. This identification is not readily adaptable to the case of wire links. Adding an information element to a wire link according to the teachings of McTiffin would require an increase in the processing capacity of network terminal equipment, such as a network termination unit (NTU). However, an increase in processing capacity of this kind would be unnecessary since is the case of a wire link, there is typically only one link between the NTU and the backbone network.

Moreover, the McTiffin technique is better suited to CDMA (Coded Division Multiple Access) or TDMA (Time Division Multiple Access) techniques which make use of cell subdivision to encapsulate an integer number of ATM cells within a radio frame. An encapsulation of this kind requires additional bandwidth for the introduction of intervals of silence between two cells intended for one and the same addressee. The approach according to McTiffin is therefore compatible solely with radio transmission systems that delineate cells in order to separate them and therefore requires technique or equipment that are specifically adapted for executing this approach. Lastly, this known approach is not compatible with the transmission of a continuous flow of cells, since their synchronization is provided by the transmission network.

It is therefore generally an object of the present invention to attempt to overcome or alleviate the various drawbacks of the prior art which were previously mentioned. More specifically, it is one of the objects of the present invention to attempt to provide a method for the transmission of data elements organized into cells (for example ATM type cells) that can be used to derive a bandwidth gain on a portion of the transmission, for instance at the ends of a transmission network. An additional object of the invention is to attempt to provide a method of this kind which may make it possible to provide additional services beyond that of the simple transmission of cells, for instance based on a standard telephone type terminal link. Examples of these additional services include those relating to leased lines, Frame Relay transmission, Internet services and other services that will be apparent to those skilled in this art.

It is another object of the invention to attempt to provide a method of the kind described above that is independent of the transmission system implemented at the level of the subscriber. In particular, an object of the invention is to seek to provide a method of this kind that could be adapted to any type of appropriate network (RF, wire, or the like).

It is a further object of the invention to seek to provide a method of the kind described above that can be used to simplify the administration of the network or at least not render it more complex. It is also an object of the invention to attempt to provide a communications system as well as a network termination unit or other apparatus for use with such a system, all of which implement a method along the lines previously described.

These objects as well as others shall become apparent from the detailed description of the present invention which follows.

SUMMARY OF THE INVENTION

According to a first broad aspect of the present invention, there is provided a method for transmission of a stream of data between two communications devices of a transmission system, the data being segmented into packets prior to transmission thereof, each of the packets comprising a header of a given size and a payload, the method comprising the steps of: (a) at a first of the two communications devices, reducing the given site of a selected number of said headers prior to said transmission of packets by eliminating a predetermined data element therefrom to thereby respectively form reduced headers; (b) transmitting each of said reduced headers from said first of the two communications devices to a second of the two communications devices; end (c) at said second of the two communications devices, restoring the given size of the selected number of said headers when each of said reduced headers so transmitted has been received by said second of the two communications devices by reconstituting each said predetermined data element.

According to a second broad aspect of the present invention, there is provided a signal representing a stream of data for transmission between two communications devices of a transmission system, the data being segmented into packets prior to transmission thereof, each of the packets comprising an originating header of a given size and a payload, the improvement characterized by a selected number of the packets comprising a transmission header of a reduced size when compared to the given size of the originating header, the reduced size being obtained by eliminating a predetermined data element from the originating header prior to transmission of the packets, and wherein the given size is restored to the transmission header by reconstituting each said predetermined data element following transmission of the packets.

According to a third broad aspect of the present invention, there is provided an apparatus for transmission of a stream of data to a communications device of a transmission system, the data being segmented into packets prior to transmission thereof, each of the packets comprising a header of a given size and a payload, the apparatus comprising a processor which reduces the given size of a selected number of said headers prior to said transmission of packets by eliminating a predetermined data element therefrom to thereby respectively form reduced headers, and wherein the given size is restored to the reduced headers when same are received by the communications device by reconstituting each said data element According to a fourth broad aspect of the present invention, there is provided an apparatus for reception of a stream of data transmitted by a communications device of a transmission system, the data being segmented into packets prior to transmission thereof, each of the packets comprising a header of a given size and a payload, the given size of a selected number of said headers having been reduced by the communications device prior to said transmission of packets by eliminating a predetermined data element therefrom to thereby form reduced headers, the apparatus comprising a processor which restores the given size of the selected number of said headers when each of said reduced headers so transmitted has been received by the apparatus by reconstituting each said predetermined data element.

With reference to illustrative embodiments of the invention, there is provided a method for the transmission of data organized in cells between two communications devices of a transmission system, each of the cells comprising a header in the form of a complete header and a payload, the method comprising a step for the reduction of the size of each of at least certain of said headers to form headers that are reduced by the elimination of predetermined data elements in said complete headers, at least some of said devices comprising means for the rebuilding of said complete headers from said reduced headers.

Thus, the invention relies on an approach which operates at the level of the transmission or reception of cells. Indeed, instead of proposing the use of more efficient means for the higher-speed transmission of fixed size cells, it is proposed to implement means for the reduction or compression of cells within the communications device for the transmission of cells and, furthermore, means for the decompression or reconstruction of the compressed cells within the communications device for the reception of the cells. It is thus not necessary to increase the required bandwidth associated with a network or its constituent network elements.

The illustrative embodiments of the invention therefore rely on the compacting of certain header fields of the transmitted cells by an elimination of data elements which are unused on the particular transmission zone or portion being traversed. It is therefore possible to increase the number of cells, and therefore the number of useful data elements, at a constant bit rate in the transmission network. In other words, the exploitable bandwidth within the communications devices, for instance those located outside the boundary of a given network domain, is increased.

It will be noted that the method according to illustrative embodiments of the invention for the transmission of data elements organized in cells is not obligatorily symmetrical or bidirectional. Thus, the method of the present invention can be implemented in only one direction of transmission, if desired. Advantageously, said step for the reduction of the size of the headers may be implemented on an end line supplying a network termination unit. However, if necessary, other transmission zones of the network domain may implement this technique.

According to another illustrative embodiment of the invention, said reduced header comprises a reduced Virtual Path Identifier (VPI) encoded on 4 bits corresponding to the 4 least significant bits of the complete Virtual Path Identifier and a reduced Virtual Channel Identifier (VCI) encoded on 8 bits corresponding to the 8 least significant bits of the complete Virtual Channel Identifier, said devices rebuilding said complete identifiers (VPI and VCI by the insertion of 4 to 8 zeros, respectively, to form the most significant bits. Thus, a reduction of 12 bits is obtained on the size of each cell by implementing the foregoing technique.

Advantageously, the Generic Flow Control (or GFC) field may also be eliminated from said reduced header, said devices rebuilding the Generic Flow Control field by the insertion of 4 zeros.

According to a further embodiment of the invention, said reduced header and said complete header may comprise an error detection end correction field, known in the ATM protocol as a Header Error Check (HEC) field, for instance encoded on 8 bits, with an associated header error control algorithm that relates only to the bits forming said reduced header. According to as advantageous variant of this or other embodiments of the present invention, said reduced header may comprise a reduced Header Error Check field, for instance of less than 8 bits, with an associated header error control algorithm that relates only to the bits that form said reduced header. Said reduced header error control field may comprise for example 5 bits and may be computed by means of a Hamming code known to those in this art.

If so desired, said reduction step may be implemented systematically in relation to two predetermined network devices on all cells transmitted therebetween. The predetermined devices in particular may be, first, a network device placed at the beginning of a line of a transmission system and second, a network device placed at the end of this line of the transmission system.

Optionally, a first of said network devices may determine the implementation of said reduction step and/or the corresponding conditions of its implementation, whether during the setting up of a link or during cell transmission or during both activities. The second of said network devices will then adopt this determination made by the, first of said devices. Advantageously, said conditions of implementation may include the selection and the size of at least one field of said reduced header. Likewise, the implementation of said reduction step and/or the conditions of its implementation may be negotiated between said network devices during transmission, as the case may be.

Advantageously, the method of the present invention described above may also comprise a step of synchronization in each of said network devices, which step consists of searching for the beginning of complete cells or reduced cells, as the case may be. This synchronization step may facilitate or enable the determination by said first device of whether to implement the reduction step mentioned previously and if so, the conditions of such implementation. In other words, the synchronization step can be utilized to enable an intermediate communications device and/or receiver of the transmitted cells to determine the choice or choices of the reduction format or formats which were made on the reduced cells by the communications device that is the sender of such cells.

An illustrative embodiment of the invention also relates to the reduced cells as such, created according to the method described hereabove. These cells each comprise a header and a payload, wherein said header comprises a reduced number of data elements, with certain of the data elements of said header being eliminated. The said cell is transmitted between two communications devices of a transmission system wherein the two devices do not use the eliminated data elements, these devices comprising means for the rebuilding of said eliminated data elements.

An illustrative embodiment of the invention, also relates to a communications system implementing the above-described method in which at least two of said devices exchange at least certain cells including a reduced header. The reduced header is obtained by the elimination of data elements from said complete header and which are not used between said devices. The devices comprise means for the rebuilding of said complete header, on the basis of said reduced header.

Other embodiments of the present invention also relate to network equipment such as a network termination unit implemented in the above-described system and comprising means for the reduction of the size of a complete header to form a reduced header and means for the rebuilding of a complete header from a reduced header.

According to another broad aspect of the present invention, a method for transmission of a stream of data between first and second communications devices of a transmission system is provided. The data is segmented into packets prior to transmission thereof. Each of the packets comprises a header of a given size and a payload. The method comprises the steps of: (a) at the first communications device, in the header in the stream of data, examining a predetermined data element and evaluating information therein to determine whether the information is available to the first and second communication devices, independently from information in other headers in the stream of data; (b) if the information is available to the first and second communication devices, reducing the given size of the header prior to the transmission of packets by eliminating the predetermined data element therefrom to form a reduced header; (c) transmitting the reduced header from the first of the two communications devices to the second communications device; and (d) at the second communications device, restoring the given size of the header when the reduced header so transmitted has been received by the second of the two communications devices by reconstituting the predetermined data element thereto.

The reconstituting of the predetermined data element may be accomplished by the insertion into the reduced header of a bit having a value of zero. Error verification of the transmitted packet may be conducted only in relation to bits forming part of the reduced header. The error verification may be accomplished by encoding the reduced header with a header error check field. The error verification may be computed by way of a Hamming code.

All headers transmitted from the first communications device may be examined. The packets may be cells of a fixed length. The cells may be Asynchronous Transfer Mode (ATM) cells.

An additional data element may be eliminated from the header. The data element and the additional data element may be comprise a Virtual Path Identifier (VPI) and a Virtual Channel Identifier (VCI). The reduced header may comprises a least significant portion of the VPI and a least significant portion of the VCI. The reconstituting of each predetermined data element may include adding a sufficient number of bits each having a value of zero to the portion of the VPI and the portion of the VCI.

The header, prior to the eliminating of the predetermined data elements therefrom, may comprises a Generic Flow Control (GFC) field. The Generic Flow Control (GFC) field may be eliminated to further form the reduced header. The reconstituting of each predetermined data element may include adding a sufficient number of bits each having a value of zero to the reduced header to reconstitute the GFC field.

The header error check field of the header prior to the eliminating of predetermined data elements therefrom and of the reduced header may be a Header Error Check (HEC) field according to the Asynchronous Transfer Mode (ATM) protocol. The header error check field of the header prior to the eliminating of predetermined data elements therefrom and of the reduced header may be a Header Error Check (HEC) field according to the Asynchronous Transfer Mode (ATM) protocol and in the case of the reduced headers may be encoded on fewer than 8 bits. The Header Error Check (HEC) field of the reduced headers may be encoded on 5 bits.

Each header to which the step of reducing is applied may be identified on instructions received by the first communications device. The predetermined data element may be identified for elimination on instructions received by the first communications device. The instructions may be furnished by the second communications device The instructions may be furnished by a network management device. The instructions may be furnished by a network management device.

The additional data element may relate to information selected from one of: a payload type; a cell loss priority; and a header error check. The stream of data may be examined for a header in on a periodic basis. The first and second communication devices may negotiate before the first communication device examines the stream of data.

According to yet another broad aspect of the present invention, an apparatus for transmission of a stream of data to a communications device of a transmission system is provided. The data is segmented into packets prior to transmission thereof. Each of the packets comprises a header of a given size and a payload. The apparatus comprises a processor which: examines the header in the stream of data; examines a predetermined data element therein; evaluates information in the header to determine whether the information is available to the apparatus and the communication device, independently from information in other headers in the stream of data; if the information is available to the apparatus and the communication device, causes the reduction the given size of the header prior to the transmission of packets by eliminating the predetermined data element therefrom to form a reduced header; and controls transmitting the reduced header from apparatus.

According to a further broad aspect of the present invention, an apparatus for reception of a stream of data transmitted by a communications device in a transmission system is provided. The data is segmented into packets prior to transmission thereof. Each of the packets comprises a header of a given size and a payload. The given size of the header having been reduced by the communications device prior to the transmission of packets by evaluating information in the header to determine whether the information is available to the communication device and the apparatus independently from information in other headers in the stream of data, and if the information is available to the communications device and the apparatus, causing the reduction of the given size of the header prior to the transmission of packets by eliminating the information therefrom to form a reduced header. The apparatus comprises: a processor which restores the given size of the header when the reduced header so transmitted has been received by the apparatus by reconstituting the eliminated information.

BRIEF DESCRIPTION OF THE DRAWINGS

By way of illustration and not of limitation, other features and advantages of the invention will become apparent from the following detailed description of illustrative embodiments of the invention given with reference to the appended drawings, in which.

DETAILED DESCRIPTION OF EMBODIMENTS OF THE INVENTION

The present invention therefore relates to a method for the transmission of data elements organized in packets or cells, which method may enable transmission under efficient conditions even when the bit rate is limited, for instance outside of the boundary of a network domain.

Hereinafter in the present description, we shall consider as an example a network of a data transmission system organized in cells according to the Asynchronous Transfer Mode (ATM) Protocol. Conventionally, a cell in ATM comprises a header used to designate the address of its addressee and a data zone or payload conveying the useful data intended for the receiver of the cell. According to the invention, the method comprises a stop to reduce the size of at least some of the headers between two communications devices of the transmission system to form reduced headers by the elimination of predetermined date elements in the complete headers, at least one of the devices comprising means for the rebuilding of the complete headers on the basis of site reduced headers.

Figure 1:
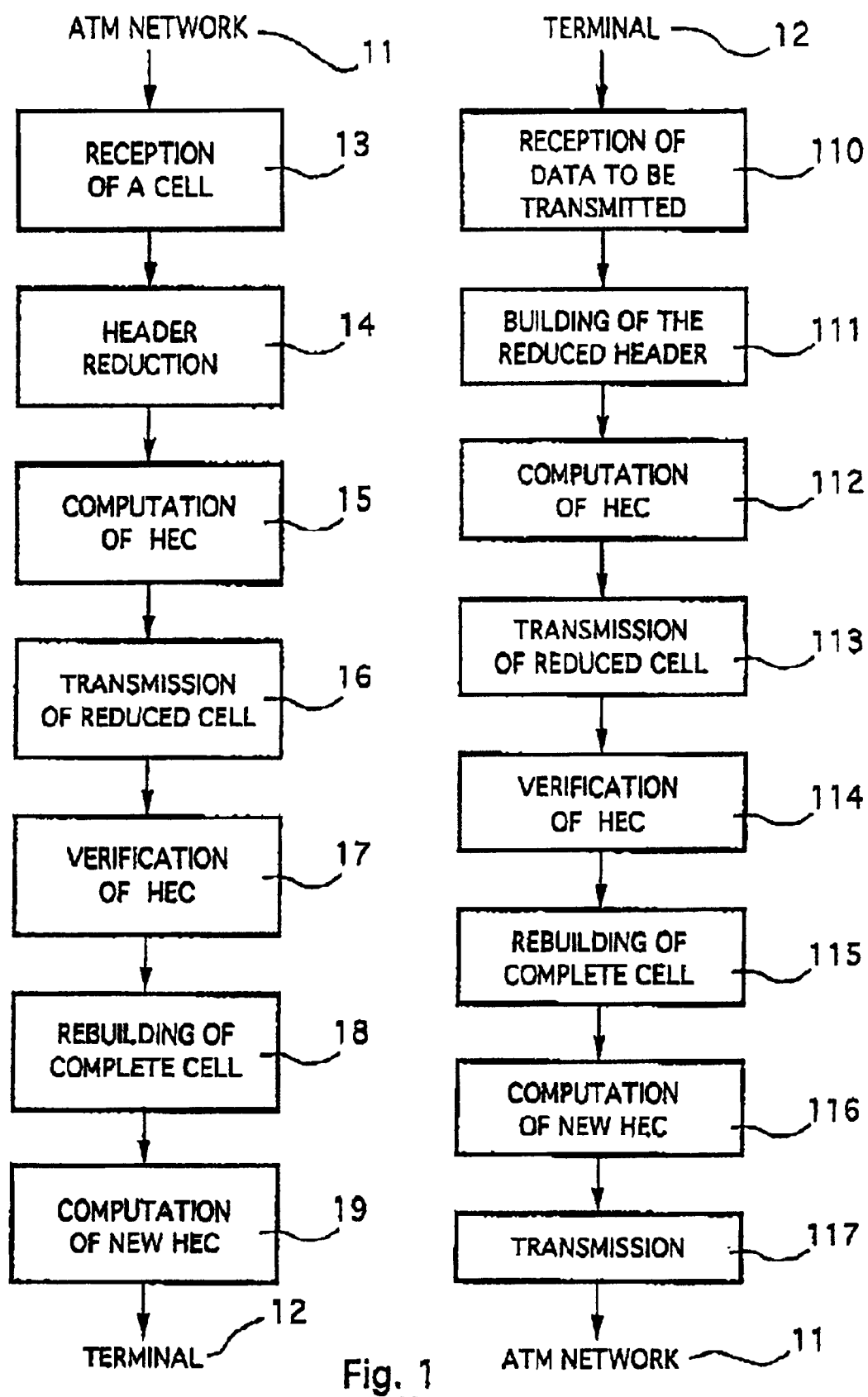
FIG. 1 is a simplified flow chart of a particular mode of implementing a method for the transmission of data elements organized in cells according to the present invention.

Referring to the flowchart of FIG. 1, a particular mode of implementation of the method according to the invention for the transmission of data organized in cells will next be presented. This particular embodiment relates to the transmission of ATM cells between an ATM network and a user terminal having a conventional transmission line therebetween. As already indicated, the method of the invention can be implemented selectively in only one direction of transmission if so desired. The flowchart of FIG. 1 shows these two directions of transmission independently.

In the direction going outbound from the ATM network 11 to the terminal 12, when a cell that has to be delivered to the terminal 12 is received at block 13 of the flowchart, its header is reduced at 14. This operation relies on the elimination, from the header of the cell, of information elements that are not ordinarily used for the transmission between the network and the terminal. Thus, the size of the header, and therefore that of the cells, is reduced. At a constant bit rate, then, it therefore becomes possible to transmit a greater number of reduced cells in a given interval of time.

In other words, the method of the invention creates available bandwidth for other cells. This freeing of bandwidth is valuable especially for those lines which provide access to networks of transmission systems and which operate at relatively low cell transmission speeds, i.e. speeds of the order of several kbits/s to about several Mbits/s. Indeed, a bandwidth gain (conventionally expressed in terms of a bit rate, namely in terms of a number of cells(s) per unit of time), even of the order of a small percentage increase, may be desirable in order to gain access to useful additional data. This access to additional data enables a more efficient exploitation of the functions available at the end user site. The end user may thus have additional services made available, while utilizing very much the same installed rated equipment and lines.

Advantageously, according to the invention, the computation of detection data and/or Header Error Check (HEC) data is done as at 15 on the data elements of the reduced header. The corresponding HEC field may also be reduced accordingly. Pursuant to another embodiment, the HEC field is kept at its initial size and in this way it enables a more efficient correction of errors because it is computed for a reduced overall number of header bits.

The reduced cell is then transmitted as at 16 from the end of the ATM network 11 to the terminal 12. A verification of the Header Error Check (HEC) field is done as at 17 on the basis of the HEC computed at step 15. In the network termination unit (NTU), the complete cell is rebuilt as at 18 by recreating therein the data elements that were previously eliminated. However, this step is not obligatory in this particular example since the cell has reached its Destination. Finally, the Header Error Check (HEC) field associated with the complete cell is computed as at 19, and the data elements obtained in the terminal 12 are delivered.

In the other inbound direction of transmission, namely from the terminal 12 to the ATM network 11, a cell with a reduced header is directly assembled as at 111 from the data elements which are received at 110 the transmission. Header Error Check (HEC) data elements are computed as a 112 on this reduced header. Next, the reduced cell is transmitted as at 113 to the desired end location within the ATM network. In the network device of the corresponding ATM network, a verification of the Header Error Check (HEC) field is done as at 114 on the basis of the HEC data elements computed in step 112. Then, the complete cell is rebuilt as at 115 by the reinsertion therein of the data elements previously eliminated from the header. With the cell having thus been rebuilt, the new Header Error Cheek (HEC) field associated with the complete cell is computed as at 116. Lastly, the complete cell is then transmitted (117) in the conventional way on the ATM network 11.

Figure 2:
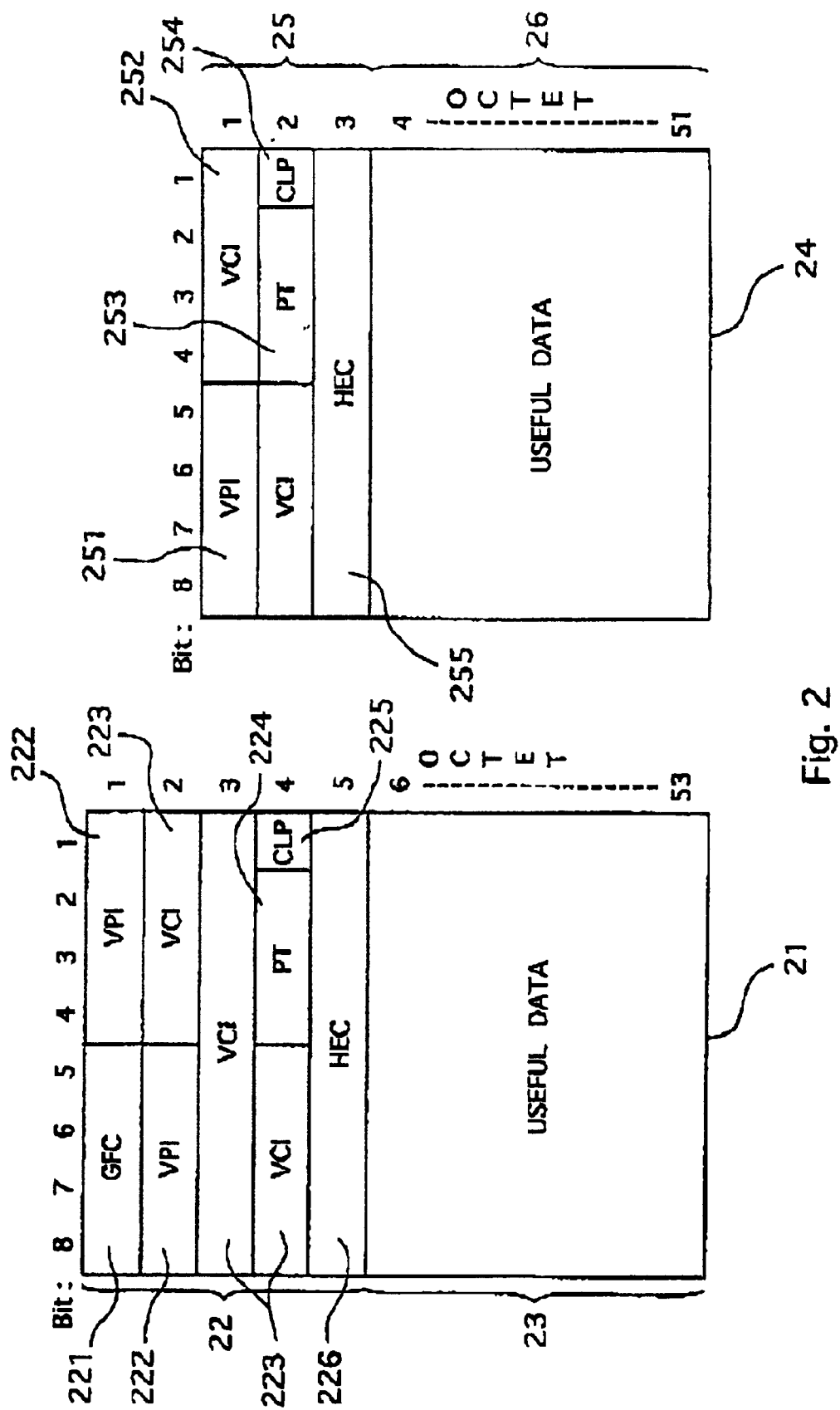
FIG. 2 is a simplified diagram of a particular embodiment of a reduced cell obtained by the implementation of the method of FIG. 1 in comparison with a complete cell of the prior art.

Referring to FIG. 2, an exemplary cell that is reduced according to the invention is presented in comparison with a complete cell according to the prior art. Conventionally, a complete cell 21 as found in the prior art comprises a header field 22 having 5 data bytes or octets pertaining to the network address of the addressee of the cell 21 and an information field or payload 23 comprising 48 bytes of useful data elements is the form of user data, signalling data or maintenance information. More specifically, the header field 22 typically comprises:

(1) a Generic Flow Control (GFC) field 221 encoded on 4 bits. This field 221 has local significance only, and is used to carry out local functions on the user site. For instance, the GFC field may allow a multiplexer to control the rate of an ATM terminal;

(ii) fields 222 and 223 which enable routing. The address field 222 is a complete Virtual Path Identifier (or VPI) field encoded on 8 bits, of which the number of useful bits may be predetermined by a network which forms part of a working transmission system and by a user of the network. The address field 223 is a complete Virtual Channel Identifier (or VCI) field encoded on 16 bits, of which the number of bits to be used may also be predetermined by a network which forms part of a working transmission system and by a user thereof;

(iii) a Payload Type or PT field 224 encoded on 3 bits. This field 224 indicates whether the complete cell 21 comprises a piece of user information or information relating to the connection associated layer management;

(iv) a Cell Loss Priority (CLP) field 225 coded on 1 bit This field 225 indicates the loss priority of an individual cell, and therefore makes it possible to discern whether the corresponding cell 21 can be discarded in the event there is a congestion within the ATM network; and (v) a Header Error Check (HEC) field 226 coded on 8 bits. This field is used by the Transmission Convergence (TC) sublayer of the Physical (PHY) layer according to the B-ISDN protocol model of ITU-T Recommendation I.321, well-known to those skilled in this art. The HEC field is implemented for the detection and correction of errors in the header field of the cell 21. This field 226 is used to perform a correction on a single-bit error and to detect multi-bit errors.

A reduced cell 24, obtained by the implementation of the method described hereabove, comprises for example a reduced header field 25 containing only 3 bytes and a information field or payload 26 that is unmodified compared to the prior art complete cell 32 (and therefore comprises 48 useful data bytes).

Unlike the complete header field 22, the reduced header field 25 does not include the Generic Flow Control (GFC) field, if so desired the communications devices themselves rebuild or recreate the Genetic Flow Control field by inserting a series of 4 consecutive zeros at the appropriate locations.

The reduced header field 25 may comprise the following fields:

(i) two fields to identify the destination:
(a) a reduced Virtual Path Identifier (VPI) field 251 encoded on 4 bits. These 4 bits correspond to the 4 least significant bits of the complete virtual path identifier field 222. In other words, the 4 most significant bits of the complete Virtual Path Identifier field 22 are eliminated;
(b) a reduced Virtual Channel Identifier (VCI) field 252 encoded on 8 bits. These 8 bits correspond to the 8 least significant bits of the complete Virtual Channel Identifier field 223. In other words, the 8 most significant bits of the complete Virtual Channel identifier 223 are eliminated.

At the reception of the reduced Virtual Path Identifier field 251 end the reduced Virtual Channel Identifier field 252, the communication devices that shall be described in detail further below rebuild the complete Virtual Path Identifier field 222 and the complete Virtual Channel Identifier field 223 by inserting 4 and 8 zeros, respectively, as most significant bits.

(ii) a Payload Type (PT) field 253 encoded on 3 bits (identical to the field 224 mentioned here above). Optionally, the Payload Type field 253 may be encoded on 2 bits. An additional data element is therefore eliminated. In this case, the communication devices rebuild the eliminated data element by the insertion of a zero as a most significant bit. Example I below presents a particular mode of encoding a set of possible values for the Payload Type field 253 and their corresponding meaning;

(iii) a Cell Loss Priority (CLP) field 254 encoded on 1 bit (identical to the above-mentioned field 225). Optionally, the Cell Lose priority field 254 may be eliminated;

(iv) a Header Error Check (HEC) field 253 located in the header field 25, encoded on 8 bits (identical to the above-mentioned field 226). The header error control algorithm used relate only to the bite forming the reduced header field 25.

According to an advantageous alternative embodiment, the header error control field 255 may have a smaller size, for instance of less than 8 bits, with the header error control algorithm used relating only to the bits that form the reduce header field 25.

The exemplary reduced cell 25 that has just been described has an integer number of bytes. However, a reduced cell may also present a number of information bits included in the header field 25 such that it does not correspond to an integer multiple of bytes while remaining within the framework of the preset invention.

A detailed description is next given of the Header Error Check field 255. The sequence of the Header Error Check field 255 is generated by dividing the information field 251 to 254 of the header 25 by a generator polynomial (H(x)). The generator polynomial chosen may be capable of detecting multiple-bit errors and of correcting errors on a single bit. The Header Error Check field 255 may also be used for cell delineation, namely to determine the beginning of a new cell corresponding to that of a new header field 25.

For example, the following is a generator polynomial associated with the reduced cell 24 corresponding to a Header Error Check field encoded on 8 bits that is sufficient for the correction of a single error:

$$1+x+x^2+x^3 \quad (1)$$

As explained below, the generator polynomial may correspond at least partly to Hamming codes generated in order to correct the transmission of an error on a single bit.

According to an alternative mode of implementation, it is possible to envisage an improved error correction in the header field 225 while maintaining the size of the Header Error Check field 255. The codes used for the correction of only one error comply with the following Harming Rule:

$$2^r - r = m+1 \quad (2)$$

where:

r is the degree of the generator polynomial and also the number of bits of the header error control field 255; and m is the number of information bits in the header field 25. Example II below sets out a first table which defines a typical correspondence between the size of the Header Error Check field 253 and that of the reduced header field 25 according to the Hamming Rule. Example II also provides a second table which presents a family of Hamming codes related to the degree of a particular generator polynomial, in Example III below, alternative generator polynomial are presented.

Hereinafter, an example is given of a reduced Header Error Check field 255 for a cell 24 comprising a reduced header field 25 with the following format:

(i) a reduced Virtual Path Identifier field 251 encoded on 2 bits;

(ii) a reduced Virtual Channel Identifies field 252 encoded on 4 bits;

(iii) a Payload Type (PT) field 253 encoded on 3 bits;

(iv) a Cell Loss Priority (CLP) field 254 encoded on 1 bit.

The number of information bits of the reduced header field 25 in the foregoing example therefore amounts to 10 in total. This, corresponds in the table of Example III to a Header Error Check field 255 of 5 bits. According to the table of Example III, the following is the generator polynomial of the Header Error Check field 255 computed by means of the Hamming code:

$$2+x^2+x^4+x^5 \quad (3)$$

This code has a Hamming distance of 4 which means that it is capable of correcting errors of only one bit. In this case, the reduced header 25 comprises 15 bits. It will be noted that this example of a reduced header does not have a number of bits that is an integer multiple of bytes. To overcome this problem, it is possible if necessary to use a sixth degree generator polynomial to obtain, for example, a reduced header field 25 encoded on 16 bits.

The header field 25 therefore comprises a reduced number of data elements since some of the data elements of the complete header field 22 have been eliminated. The gain in cell space which is obtained according to the technique described above corresponds to a bandwidth gain that can be expressed according to the following formula:

$$Gb = 100 - (l_R * 100)/(l_C) \quad (4)$$

where;

Gb Is the bandwidth gain;

$l_R$ is the length of the reduced cell 244 in bits; and $l_C$ is the length of the complete cell 21 in bits.

In the example described with reference to FIG. 2, the bandwidth gain amounts to 3.77% according to the foregoing formula (4). On the other band, with an exemplary reduced cell having the following format:

(i) a Virtual Path Identifier (VPI) field encoded on 2 bits;

(ii) a Virtual Channel Identifier (VCI) field encoded on 4 bits;

(iii) a Payload Type (PT) field encoded on 3 bits;

(iv) a Cell Loss Priority (CLP) field encoded on 1 bit;

(v) a Header Error Check (HEC) field encoded on 8 bits;

(vi) a payload field encoded on 48 bytes;

a bandwidth gain of 5.89% may be obtained according to formula (4) set out above.

The reduced cell 24 is transmitted between two communications devices of a transmission system, namely a sender communications device and a receiver communications device. As shall be seen herebelow, thus communications devices comprise means for the rebuilding of the eliminated data dements, for instance by inserting zeros at the locations affected by the elimination of data elements.

Figure 3:
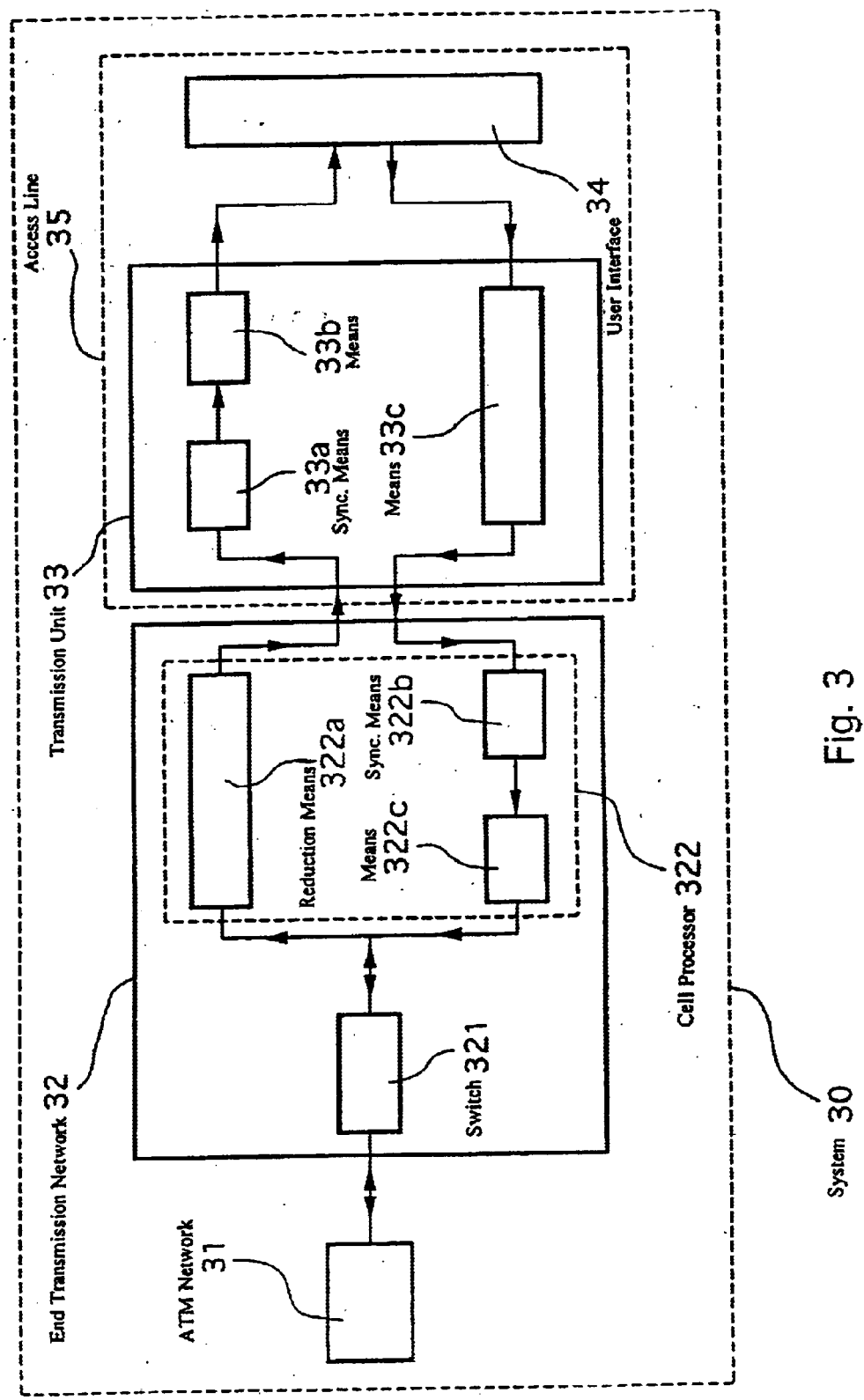
FIG. 3 is a simplified diagram of a particular embodiment of a network forming part of a transmission system capable of implementing the method of FIG. 1.

With reference to the simplified drawing of FIG. 3, a particular embodiment of a network forming pats of a communications system 30 for the transmission of reduced cells according to the invention is next presented. In a standard way, an ATM network 31 is connected to an end transmission network 32 with which it exchanges data elements organized in the form of complete cells according to a fixed bit rate, for example of the order of several Mbits/s. The end transmission network 32 may be of the wire type implementing an SDSL technique. It will be noted, however, that the method of the invention is compatible with any type of transmission network. In particular, it may relate to DSL, ADSL, HDSL or other types of transmission networks.

The end transmission network 32 comprises a plurality of switching means, such as switch 321 or an ATM access MUX, which manage a plurality of transmission systems ending in user interfaces. With a view to simplification, only one transmission system comprising the transmission network 32, a network termination unit 33 and a user interface 34 has been shown in FIG. 3. The step of reducing the size of the cell headers as described above in relation to the method of the present invention is implemented on an end line network or ATM access line 35 that feeds the network termination unit 33.

The switch 321 manages signals transmitted in the outbound direction, namely from the end transmission network 32 to the user interface 34 and also signals received in the inbound direction, namely from the user interface 34 to the end transmission network 32. In general the direction of the signals exchanged is symbolized in FIG. 3 by an arrow pointing in the direction taken by the signals on the transmission system. The user interface 34 may, for example, be a device compatible with the Asynchronous Transfer Mode (ATM) protocol, an interface not compatible with the ATM protocol such as a Frame Relay interface, a circuit interface (T1, E1, V35, and the like) or an Ethernet interface using ATM adaptation layers on top of lower order ATM protocol layers.

A description will first be given of the means implemented in the outbound direction within the transmission system 30. The ATM network 31 delivers complete cells according to the prior art to the switch 321. On the associated end transmission system, the switch 321 routes the complete cells that it receives as a function of the address contained in the header field of the complete cells. According to an alternative embodiment, and as alluded to above, the switch 321 may be replaced by a multiplexing device which selects a given transmission system from among several transmission systems as a function of the address contained in the header field of the complete cells that it receives.

The switch 321 delivers the complete cells to a cell processor 322 that includes means 322a for the reduction of the size of at least certain complete herders of the complete cells. These reduction means 322a eliminate the unused data elements of at least one field included in the complete header field of certain complete cells received so as to form reduced headers in order to build reduced cells.

Advantageously, when a link is set up and/or during transmission, the cell processor 322 may be provisioned to determine the implementation or frequency of the reduction step (i.e. whether or not to reduce a given cell) and/or the corresponding conditions of such implementation (i.e. selection of the data fields to be reduced or eliminated, and determining the resulting size of the selected data field in the case the field is not entirety eliminated). This makes it possible to manage the resulting bandwidth gains more efficiently as a function of the available needs and resources of the communications network. The conditions of implementation of the reduction step may comprise, for example, the size of the different fields that are to be retained in the header field of the reduced cells.

According to an alternative embodiment, the implementation of the reduction step, its frequency of implementation with respect to received calls and/or the conditions associated with implementation of the reduction step may be negotiated or otherwise determined by the cell processor 322 and the network termination unit 33 during cell transmission. An implementation of this kind may be executed for instance in software by a modification of the logic associated with the cell processor 322 and the network termination unit 33. Consideration may also be given to making use of higher layers in the ATM protocol in order to provide the necessary intelligence for such an implementation. Such negotiation may, for instance, take the form of a handshake between the two devices at the management layer level. To communicate the handshake, a dedicated ATM cell may be used or network management may be resorted to. A scheme of negotiation would make it possible to adapt the enablement of cell header reduction or the extent to which it tastes place to the performance characteristics of the corresponding network termination unit 33 and to take account of its state of congestion in terms of enlarged cells.

According to as alternative embodiment, the step of reducing the size of the headers is implemented systematically on all cells transmitted between the cell processing means 322 of the transmission network 32 and the network termination unit 33.

The reduction means 322a provides the network termination unit 33 with a stream of reduced cells or a stream comprised of both reduced cells and complete cells. The network termination unit 33 comprises:

(i) a synchronization means 33a that seeks the beginning of the complete cells and/or reduced cells. This synchronization means 33a makes it possible for instance to discern the actions taken on any given transmitted cell by the cell processor 322; and (ii) a means 33b for the rebuilding or reconstruction of the reduced cell headers into complete headers. This reconstruction is accomplished by inserting zeros at the places of the eliminated data elements within reduced header fields of the affected cells and by recomputing the Header Error Check (HEC) field 226 associated with a reconstructed complete header field.

Optionally, it is possible to provide for additional means of bit synchronization. These bit synchronization means would make it possible to locate a particular data field within a header element. This may make it possible in particular to locate the places where the elimination of data elements has been done beforehand, and to perform a filling of data elements in order to rebuild the complete cells.

The mean 336 for the rebuilding of the headers delivers complete cells to the user interface 34. This user interface 34 may therefore receive a greater number of useful date elements than would be the case if it received only complete cells. This would enable it to implement, for example simultaneously, additional services such as one or more leased line services, one or more Frame Relay services and/or one or more services related to the Internet.

It will be noted that any equipment or devices implemented outbound from the communications device 33 require no modification to be able to process the reduced cells, since the receiver communications equipment 33 of the reduced cells is fitted out with means for the rebuilding of the complete headers providing for the reconversion of reduced cells into complete cells.

A description is next given of the means implemented in the inbound direction within the transmission system 30. It will be assumed here that the user interface 34 can send data elements organized in the form of complete cells to the data transmission network 32. To do so, on an end line, the user interface 34 supplies complete cells to the network termination unit 33. According to another embodiment of the present invention, the user interface 34 may be provisioned to supply reduced cells directly.

The network termination unit 33 comprises means 33c for the reduction of the size of at least certain of the complete headers which are received by the network termination unit 33. These reduction means 33c eliminate the unused data elements, for example under the same conditions as those implemented in the outbound direction, namely within the header field of the complete cells, so as to form reduced headers and thus supply reduced cells to the rest of the network. The reduction means 33c delivers reduced cells to the cell processing means 322 of the transmission network 32.

Advantageously, in the inbound direction the cell processor 322 comprises:

(i) a synchronization means 322b. During the origination of a transmission and/or during the course of transmission, the synchronization means 322b identifies the beginning of each received cell, thereby enabling the synchronization means 322b to determine the actions which were taken by the network termination unit 33, if any, in its implementation of the step for reducing the size of the cell headers;

(ii) a means 322c for the rebuilding of the complete headers. This means 322c for the rebuilding of the complete headers reconstructs complete cells from the reduced headers of the reduced cells by inserting zeros at appropriate places in the header, and also recomputes the Header Error Check (HEC) field associated with the reconstructed complete header field.

The rebuilding means 322c delivers complete cells to the switch 321. This switch, depending on the addressee that are included in the header field of the complete cells, feeds the appropriate transmission system or associated port.

Figure 4:
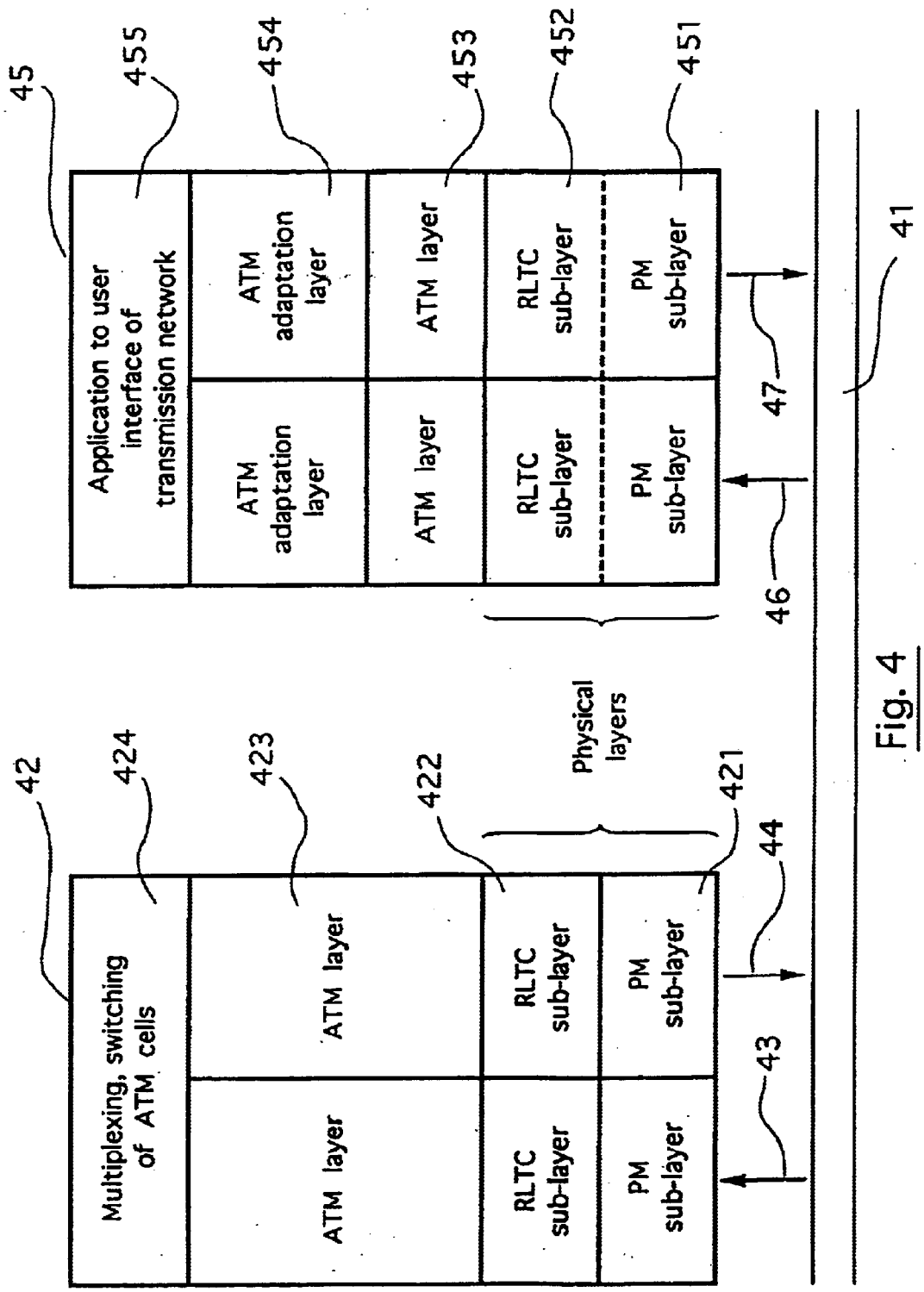
FIG. 4 is a simplified diagram of protocol model showing two protocol stacks for adopting the method of FIG. 1.

With reference to the simplified protocol stack diagrams of FIG. 4, a particular embodiment of a protocol model for adopting the method according to the invention for the transmission of data organized as cells is next presented. For purposes of illustration, it will be assumed that the invention implements a transmission network 41 operating at a relatively low bit rate of the order of several Mbits/s.

Conventionally, within the end transmission network 32, a protocol stack may provide for numerous functions 42. These functions 42 generally comprise, identically for the outbound direction 43 and inbound direction 44.

(i) a known ATM presentation layer 423 (defining for instance the exchanged information);

(ii) a known ATM application layer 424 (defining for instance the mechanisms common to the applications and the meaning attributed to the data being exchanged). Mechanisms defined in this layer may include multiplexing and ATM cell switching, to name but some examples.

These functions 423, 424 are known to those skilled in this art and shall not be described in greater detail.

The protocol stack 42 also comprises a known Physical Medium (PM) sub-layer 421 that carries out functions in relation to the physical transmission medium (namely on the transmission network 41 and end line network 35). This function 421 is also known to those skilled in the art and shall therefore not be described in additional detail. The protocol stack 42 comprises a second physical sub-layer which is a reduced cell transmission convergence (RCTC) sub-layer 422 that is integrated between the known PM sub-layer 421 and the known AN layer 423, According to the invention, this second physical sub-layer 422 enables the conversion of the flow of complete cells reaching the known ATM layer 423 into a flow of reduced cells that can be transmitted to the known PM sub-layer 421. This corresponds to the steps 13, 14 and 15 of FIG. 1. Likewise, the second physical sub-layer 422 enables the conversion of the flow of reduced cells received by the known PM sub-layer 421 into a flow of complete cells transmitted to the known ATM lays 423. This corresponds to steps 114, 115 and 116 of FIG. 1.

Furthermore, it will be noted that the reduced cell transmission convergence (RCTC) physical sub-layer 422 makes use the some techniques as a standard transmission convergence (TC) physical sub-layer defined by the existing ATM protocols as known to those skilled in the art (this existing TC sub-layer being located between the known ATM sub-layer and the known physical medium (PM) sub-layer).

Conventionally, within the end line network 35, a protocol stack 45 maybe implemented. The protocol stack 45 provides functions which may generally comprise, in a symmetrical way for both the outbound direction 46 and the inbound direction 47:

(i) a known ATM presentation layer 453 (defining for instance the information exchanged);

(ii) a known ATM adaptation layer (AAL) 454;

(iii) an application layer 455 (defining the mechanisms common to the applications and the meaning of the exchanged data) in support of applications which are associated with the user interface 34 of the transmission network.

These functions 453, 454, 455 are known to those skilled in this art and shall not be described in greater detail.

Again in a conventional way, the protocol stack 45 comprises a known Physical Medium (PM) sub-layer 451 that fulfills functions relating to the physical transmission medium. This function 451 is also known to those skilled in the art and shall therefore not be described in further detail. The protocol stack 45 comprises a reduced cell transmission convergence (RCTC) physical sub-layer 452 that is integrated between the known FM sub-layer 451 and the ATM presentation layer 453. According to the invention, this ROTC physical sub-layer enables the conversion of the flow of complete cells reaching the known ATM presentation layer 453 into a flow of reduced cells that can be transmitted to the known PM sub-layer 451. This corresponds to steps 111, 112 end 113 of FIG. 1. Likewise, the RCTC physical sub-layer enables the conversion of reduced cells received by the known PM sub-layer 451 into a flow of complete cells that can be transmitted to the known ATM presentation layer 453. This corresponds to steps 17, 18 and 19 of FIG. 1. It will be noted that this reduced cell transmission convergence RCTC physical sub-layer 422 also utilizes the same techniques as a conventional transmission convergence (TC) physical sub-layer defined by the ATM standards as known to those versed in this art.

It should be noted that no modification of the application layer 455 or of the ATM cell adaptation layer 454 or of the ATM presentation layer 453 need be done to implement the teachings of the present invention. This should enable the relatively easy adoption of the method of the invention to a network device, such as the network termination unit previously described.

Those skilled in this art will appreciate that various modification of detail may be made to the present invention, all of which would come within its spirit and scope.

EXAMPLE I

Particular Mode of Implementing the Encoding of the Reduced Cell Payload Type (PT) Field 259

The table herebelow illustrates a particular mode of implementation for possible codes of the Payload Type (PT) field 253 of a reduced header 25 and the associated meaning which may be assigned to each of these codes.

| CODING OF PAYLOAD TYPE FIELD 253 (the most significant bit being placed first) | MEANING |
| --- | --- |
| 00 | User Data Cell, Service Data Unit type = 0 |
| 01 | User Data Cell Service Data Unit type = 1 |
| 10 | Cell relating to Operation, Administration, Maintenance (OAM) F5 flow - segment associated cell |
| 11 | Cell relating to Operation, Administration, Maintenance (OAM) F5 flow - end-to-end associated cell |

EXAMPLE II

Particular Mode of Implementing Various Header Sizes which Meet the Hamming Rule A table is presented herebelow that maps various header sizes to a given maximum size of the header information field and an associated size for the HEC field 255 according to the Hamming Rule.

| Maximum bit size of the header information field (corresponding to "m" in the Hamming Rule) | 1 | 4 | 11 | 26 | 57 | 120 |
|---|---|---|---|---|---|---|
| Header Error Check (HEC) field 255 enabling the protection of the information field whose size is smaller than or equal to m, corresponding to "r" in the Hamming Rule | 2 | 3 | 4 | 5 | 6 | 7 |
| Maximum bit size of the header corresponding to "m" + "r" as these variables are defined above | 3 | 7 | 15 | 31 | 63 | 127 |

It will be noted that the number of information bits of the header field may not correspond identically with a given combination along the lines of the above associated values. In other words, for a given header field size, a non-integer value of "r" may be produced by the Hamming Rule, in such cases, it is necessary to choose a number of bits for the header control field 255 (designated by "r" is the Hamming Rule), that is the next integer value immediately greater than the non-integer value "r" that would comply with the Hamming Rule.

The following table shows a family of Hamming codes corresponding to the degree of generator polynomial ranging from 3 to 7.

| Degree (r) of the Generator Polynomial | Generator Polynomial H(x) |
|---|---|
| 3 | $1 + x + x^3$ |
| 4 | $1 + x + x^4$ |
| 5 | $1 + x^2 + x^5$ |
| 6 | $1 + x + x^6$ |
| 7 | $1 + x^3 + x^7$ |
| 7 | $1 + x^2 + x^3 + x^4 + x^5 + x^6 + x^7$ |

If two errors occur, then the correction algorithm will introduce a third error. One way to guard against this is to be capable of detecting odd numbers of errors. This may be accomplished, for example, by multiplying the generator polynomial developed hereabove by the value (1+x). This increases the number of bit verifications by one unit so that the maximum number of information elements of the reduced header field must simultaneously be reduced by one unit to maintain compliance with the Abramson Code Theory, known to those in this art. The Hamming Rule then becomes the following: $2^r - r = m + 2$, this formula being hereinafter called the modified Hamming Rule, To the extent possible, the generator polynomials of the Header Error Check field 255 must correspond to the number of information bits of the reduced header field.

EXAMPLE III

Particular Modes of Implementation of Various Header Sizes with Associated Generator Polynomials which Meet the Modified Hamming Rule The following table maps various header sizes to a given maximum size of the header information field and to associated size for the HEC field 255, together with a sample generator polynomial according to the modified Hamming Rule introduced in Example II above.

| Number of bits in the Header Error Check field 255 enabling the protection of information elements whose size is smaller than or equal to "m", corresponding to "r" in the modified Hamming Rule (see Example II) | 4 | 5 | 6 | 7 | 8 | 8 |
|---|---|---|---|---|---|---|
| Example of generator polynomial $(1 + x)*H(x)$ | $1 + x^2 + x^3 + x^4$ | $1 + x^2 + x^4 + x^5$ | $1 + x + x^2 + x^3 + x^5 + x^6$ | $1 + x^2 + x^6 + x^7$ | $1 + x + x^3 + x^4 + x^7 + x^8$ | $1 + x + x^2 + x^8$ (ATM protocol) |
| Bit size of the header equal to "m" + "r" | 7 | 15 | 31 | 63 | 127 | 127 |
| Maximum bit size of the header information field corresponding to "m" in the modified Hamming Rule (see Example II) | 3 | 10 | 25 | 56 | 119 | 119 |

What is claimed is:

1. A method for transmission of a stream of data between first end second communications devices of a transmission system, the data being segmented into packets prior to transmission thereof, each of the packets comprising a header of a given size and a payload, the method comprising the steps of:
    (a) at said first communications device, in the header in the stream of data, examining a predetermined date element and evaluating information therein to determine whether said information is available to said first and second communication devices, independently from information in other headers in the stream of data;
    (b) if said information is available to said first and second communication devices, reducing the given size of the header prior to said transmission of packets by eliminating the predetermined data element therefrom to form a reduced header,
    (c) transmitting said reduced header from said first of the two communications devices to said second communications device, and
    (d) at said second communications device, restoring the given size of the said header when said reduced header so transmitted has been received by said second of the two communications devices by reconstituting said predetermined data element thereto.

2. The method of transmission according to claim 1, wherein the reconstituting of said predetermined data element is accomplished by the insertion into the reduced header of a bit having a value of zero.

3. The method of transmission according to claim 2, wherein error verification of the transmitted packet is conducted only in relation to bits forming part of the reduced header.

4. The method of transmission according to claim 3, wherein the error verification is accomplished by encoding the reduced header with a header error check field.

5. The method of transmission according to claim 4, wherein the error verification is computed by way of a Hamming code.

6. The method of transmission according to claim 5, wherein all headers transmitted from said first communications device are examined.

7. The method of transmission according to claim 5, wherein the packets are cells of a fixed length.

8. The method of transmission according to claim 7, wherein the cells are Asynchronous Transfer Mode (ATM) cells.

9. The method of transmission according to claim 8, wherein
- an additional data element is eliminated from said header; said data element and said additional data element comprise a Virtual Path Identifier (VPI) and a Virtual Channel Identifier (VCI);
- said reduced header comprises a least significant portion of said VPI and a least significant portion of said VCI; and
- the reconstituting of each predetermined data element includes adding a sufficient number of bits each having a value of zero to the portion of said VPI and the portion of the VCL.

10. The method of transmission according to claim 9, wherein
- the header, prior to said eliminating of predetermined data elements therefrom, comprises a Generic Flow Control (GFC) field, the Generic Flow Control (GFC) field being eliminated to further form said reduced header, and the reconstituting of each predetermined data element includes adding a sufficient number of bits each having a value of zero to the reduced header to reconstitute said GFC field.

11. The method of transmission according to claim 10, wherein the header error check field of said header prior to said eliminating of predetermined data elements therefrom and of said reduced header is a Header Error Check (HEC) field according to the Asynchronous Transfer Mode (ATM) protocol.

12. The method of transmission according to claim 10, wherein the header error check field of said header prior to said eliminating of predetermined data elements therefrom and of said reduced header is a Header Error Check (HEC) field according to the Asynchronous Transfer Mode (ATM) protocol and in the case of the reduced headers is encoded on fewer than 8 bits.

13. The method of transmission according to claim 11, wherein the Header Error Check (HEC) field of the reduced headers is encoded on 5 bits.

14. The method of transmission according to claim 13, wherein each header to which the step of reducing is applied is identified on instructions received by the first communications device.

15. The method of transmission according to claim 13, wherein the predetermined data element is identified for elimination on instructions received by the first communications device.

16. The method of transmission according to claim 14, wherein said instructions are furnished by the second communications device.

17. The method of transmission according to claim 14, wherein the said instructions are furnished by a network management device.

18. The method of transmission according to claim 15, wherein the said instructions are famished by a network management device.

19. The method of transmission according to claim 9, wherein said additional data element relates to information selected from one of: a payload type; a cell loss priority; and a header error check.

20. The method of transmission according to claim 9, wherein said stream of data is examined for a header in on a periodic basis.

21. The method of transmission according to claim 9, wherein said first and second communication devices negotiate before said first communication device examines said stream of data.

22. An apparatus for transmission of a stream of data to a communications device of a transmission system, the data being segmented into packets prior to transmission thereof, each of the packets comprising a header of a given size and a payload, the apparatus comprising a processor which
- examines the header in the stream of data;
- examines a predetermined data element therein;
- evaluates information in said header to determine whether said information is available to said apparatus and said communication device, independently from information in other headers in the stream of data;
- if said information is available to said apparatus and said communication device, causes the reduction the given size of the header prior to said transmission of packets by eliminating the predetermined data element therefrom to form a reduced header; and
- controls transmitting said reduced header from apparatus.

23. An apparatus for reception of a stream of data transmitted by a communications device in a transmission system, the data being segmented into packets prior to transmission thereof, each of the packets comprising a header of a given size and a payload, the given size of said header having been reduced by the communications device prior to said transmission of packets by evaluating information in said header to determine whether said information is available to said communication device and said apparatus independently from information in other headers in the stream of data, and if said information is available to said communications device and said apparatus, ceasing the reduction of the given size of the header prior to said transmission of packets by eliminating the said information therefrom to form a reduced header, the apparatus comprising a processor which restores the given size of said header when said reduced header so transmitted has been received by the apparatus by reconstituting said eliminated information.

* * * * *

UNITED STATES PATENT AND TRADEMARK OFFICE
CERTIFICATE OF CORRECTION

| | | |
|---|---|---|
| PATENT NO. | : 6,917,616 B1 | Page 1 of 6 |
| APPLICATION NO. | : 09/397849 | |
| DATED | : July 12, 2005 | |
| INVENTOR(S) | : Dominique Normand et al. | |

It is certified that error appears in the above-identified patent and that said Letters Patent is hereby corrected as shown below:

1. On title page Item [57] Abstract, line 4: Replace the semi-colon " ; " with a colon -- : --.

2. On title page Item [56] Abstract, line 5: Delete the semi-colon -- ; --.

3. Specification, column 1, line 28: Replace the word " element " with the word -- elements --.

4. Specification, column 1, line 33: Replace the word " leader " with the word -- header --.

5. Specification, column 1, line 51: Replace the word " comes " with the word -- connects --.

6. Specification, column 2, line 16: Replace the word " is " with the word -- in --.

7. Specification, column 3, line 9: Replace the word " site " with the word -- size --.

8. Specification, column 3, line 14: Replace the " end " with the word -- and --.

9. Specification, column 4, line 56: Replace the word " end " with the word -- and --.

10. Specification, column 4, line 60: Replace the word " as " with the word -- an --.

11. Specification, column 6, line 3: Replace the word " communication " with the word --communications --.

12. Specification, column 6, line 6: Replace the word " communication " with the word --communications --.

13. Specification, column 6, line 31: Delete the word -- be --.

14. Specification, column 6, line 32: Replace the word " comprises " with the word -- comprise --.

15. Specification, column 6, line 39: Replace the word " comprises " with the word -- comprise --.

16. Specification, column 7, line 2: Delete the word -- in --.

UNITED STATES PATENT AND TRADEMARK OFFICE
CERTIFICATE OF CORRECTION

PATENT NO. : 6,917,616 B1
APPLICATION NO. : 09/397849
DATED : July 12, 2005
INVENTOR(S) : Dominique Normand et al.

It is certified that error appears in the above-identified patent and that said Letters Patent is hereby corrected as shown below:

17. Specification, column 7, line 4: Replace the word " communication " with the word -- communications --.

18. Specification, column 7, line 17: Replace the word " communication " with the word -- communications --.

19. Specification, column 7, line 18: Insert the word -- of -- after the word " reduction ".

20. Specification, column 7, line 21: Insert the word -- said -- before the word " apparatus ".

21. Specification, column 7, line 32: Replace the word " communication " with the word -- communications --.

22. Specification, column 8, line 11: Replace the word " stop " with the word -- step --.

23. Specification, column 8, line 14: Replace the word " date " with the word -- data -- .

24. Specification, column 8, line 16: Replace the word " site " with the word -- the -- .

25. Specification, column 9, line 3: Replace the word " Destination " with the word -- destination --.

26. Specification, column 9, line 10: Replace the word " the " with the word -- for -- .

27. Specification, column 9, line 11: Replace the word " a " with the word -- at -- .

28. Specification, column 9, line 20: Replace the word " Cheek " with the word -- Check -- .

29. Specification, column 10, line 7: Replace the number " 32 " with the number -- 21 -- .

30. Specification, column 10, line 11: Replace the word " Genetic " with the word -- Generic -- .

31. Specification, column 10, line 29: Replace the word " identifier " with the word -- Identifier --.

UNITED STATES PATENT AND TRADEMARK OFFICE
CERTIFICATE OF CORRECTION

| | | |
|---|---|---|
| PATENT NO. | : 6,917,616 B1 | |
| APPLICATION NO. | : 09/397849 | |
| DATED | : July 12, 2005 | |
| INVENTOR(S) | : Dominique Normand et al. | |

It is certified that error appears in the above-identified patent and that said Letters Patent is hereby corrected as shown below:

32. Specification, column 10, line 31: Replace the word " end " with the word -- and -- .

33. Specification, column 10, line 50: Replace the word " Lose " with the word -- Loss -- and replace the word " priority " with the word -- Priority --.

34. Specification, column 10, line 52: Replace the number " 253 " with the number -- 255 -- .

35. Specification, column 10, line 61: Replace the word " reduce " with the word -- reduced -- .

36. Specification, column 10, line 67: Replace the word " preset " with the word -- present -- .

37. Specification, column 11, line 24: Replace the word " Harming " with the word -- Hamming --.

38. Specification, column 11, line 33: Replace the number " 253 " with the number -- 255 -- .

39. Specification, column 11, line 36: Insert a period -- . -- after the word " polynomial " and replace the word " in " with the word -- In --.

40. Specification, column 11, line 44: Replace the word " Identifies " with the word -- Identifier --.

41. Specification, column 12, line 10: Replace the number " 244 " with the number -- 24 -- .

42. Specification, column 12, line 14: Replace the word " band " with the word -- hand -- .

43. Specification, column 12, line 29: Replace the word " thus " with the word -- these -- .

44. Specification, column 12, line 31: Replace the word " dements " with the word -- elements -- .

45. Specification, column 12, line 34: Replace the word " pats " with the word -- part -- .

UNITED STATES PATENT AND TRADEMARK OFFICE
CERTIFICATE OF CORRECTION

| | |
|---|---|
| PATENT NO. | : 6,917,616 B1 |
| APPLICATION NO. | : 09/397849 |
| DATED | : July 12, 2005 |
| INVENTOR(S) | : Dominique Normand et al. |

It is certified that error appears in the above-identified patent and that said Letters Patent is hereby corrected as shown below:

46. Specification, column 13, line 19: Replace the word " herders " with the word -- headers -- .

47. Specification, column 13, line 31: Replace the word " entirety " with the word -- entirely -- .

48. Specification, column 13, line 55: Replace the word " tastes " with the word -- takes -- .

49. Specification, column 13, line 58: Replace the word " enlarged " with the word -- exchanged -- .

50. Specification, column 13, line 59: Replace the word " as " with the word -- an -- .

51. Specification, column 14, line 20: Replace the number " 336 " with the number -- 33b -- .

52. Specification, column 14, line 22: Replace the word " date " with the word -- data --.

53. Specification, column 15, line 39: Replace the word " AN " with the word -- ATM -- .

54. Specification, column 15, line 48: Replace the word " lays " with the word -- layer -- .

55. Specification, column 15, line 52: Replace the word " some " with the word -- same -- .

56. Specification, column 16, line 33: Replace the word " AN " with the word -- ATM -- .

57. Specification, column 16, line 18: Replace the word " end " with the word -- and -- .

58. Specification, column 16, line 36: Replace the word " modification " with the word -- modifications -- .

59. Specification, column 16, line 40: Replace the number " 259 " with the number -- 253 -- .

UNITED STATES PATENT AND TRADEMARK OFFICE
CERTIFICATE OF CORRECTION

| | |
|---|---|
| PATENT NO. | : 6,917,616 B1 |
| APPLICATION NO. | : 09/397849 |
| DATED | : July 12, 2005 |
| INVENTOR(S) | : Dominique Normand et al. |

It is certified that error appears in the above-identified patent and that said Letters Patent is hereby corrected as shown below:

60. Specification, column 16, line 63: Replace the word " Mode " with the word -- Modes -- .

61. Specification, column 17, line 21: Insert a period -- . -- after the word " Rule " and replace the word " in " with the word -- In --.

62. Claim 1, column 18, line 42: Replace the word " date " with the word -- data -- .

63. Claim 1, column 18, line 45: Replace the word " communication " with the word -- communications -- .

64. Claim 1, column 18, line 48: Replace the word " communication " with the word -- communications -- .

65. Claim 20, column 20, line 16: Delete the word " in " .

66. Claim 21, column 20, line 19: Replace the word " communication " with the word -- communications -- .

67. Claim 21, column 20, line 20: Replace the word " communication " with the word -- communications -- .

68. Claim 22, column 20, line 32: Replace the word " communication " with the word -- communications -- .

69. Claim 22, column 20, line 35: Replace the word " communication " with the word -- communications -- .

70. Claim 22, column 20, line 35: Insert the word -- of -- after the word " reduction " .

71. Claim 22, column 20, line 39: Insert the word -- said -- after the word " from " .

72. Claim 23, column 20, line 48: Replace the word " communication " with the word -- communications -- .

UNITED STATES PATENT AND TRADEMARK OFFICE
CERTIFICATE OF CORRECTION

PATENT NO.        : 6,917,616 B1
APPLICATION NO.   : 09/397849
DATED             : July 12, 2005
INVENTOR(S)       : Dominique Normand et al.

It is certified that error appears in the above-identified patent and that said Letters Patent is hereby corrected as shown below:

73. Claim 23, column 20, line 51: Replace the word " ceasing " with the word -- causing -- .

74. Claim 23, column 20, line 53: Delete the word " the " .

Signed and Sealed this

Third Day of April, 2007

JON W. DUDAS
*Director of the United States Patent and Trademark Office*